Figure 1:
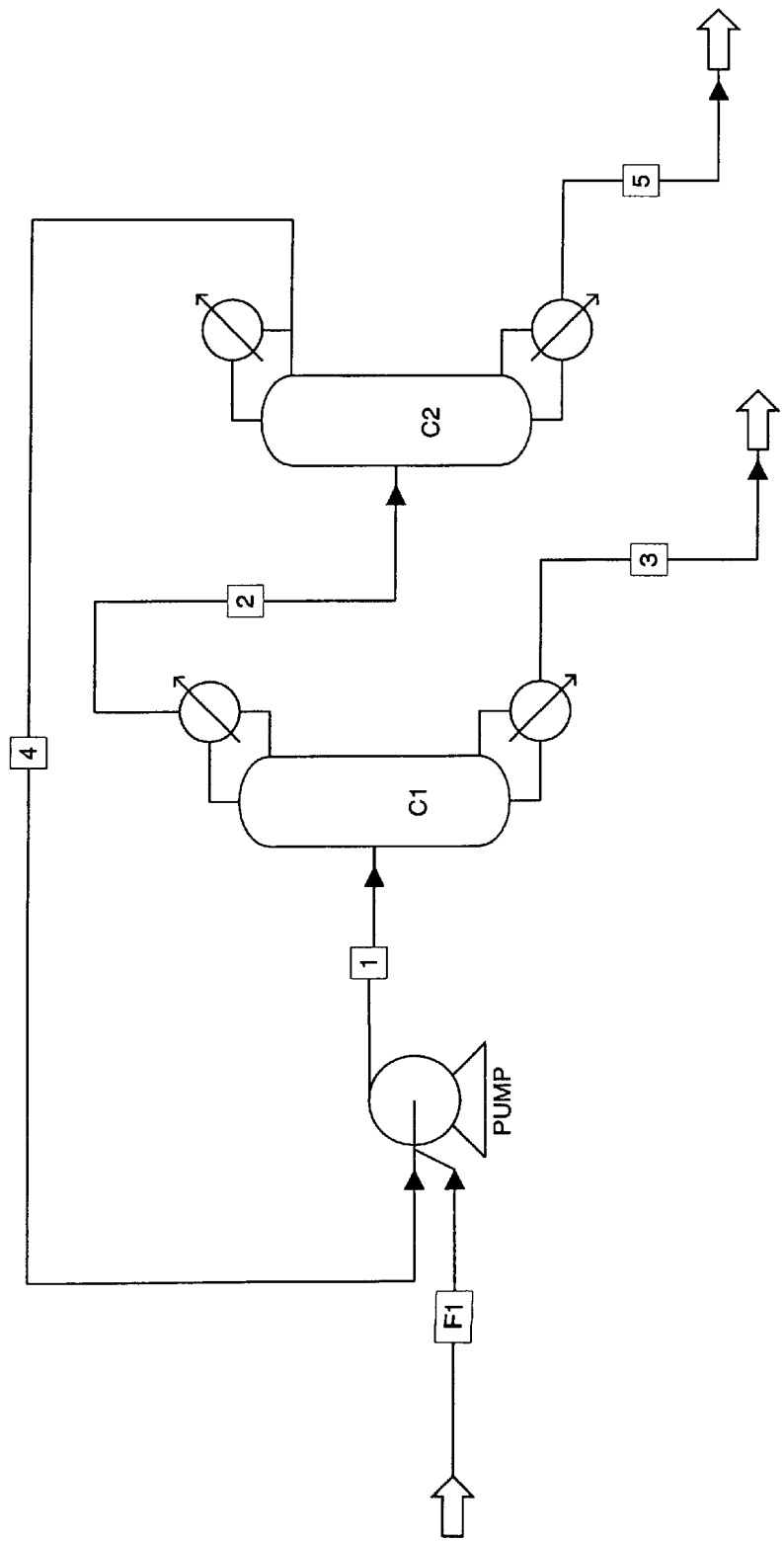

ID=1 />

United States Patent [19]
Pham et al.

[11] Patent Number: 5,918,481
[45] Date of Patent: Jul. 6, 1999

[54] PROCESS FOR SEPARATING HYDROGEN FLUORIDE FROM FLUOROCARBONS

[75] Inventors: Hang Thanh Pham; Rajiv Ratna Singh; Hsueh Sung Tung; Daniel Christopher Merkel, all of Erie County, N.Y.; David Goldschmidt, Bergen County, N.J.; Tadeusz Piotr Rygas, Ottawa, Canada

[73] Assignee: AlliedSignal Inc., Morristown, N.J.

[21] Appl. No.: 08/974,935

[22] Filed: Nov. 20, 1997

[51] Int. Cl.$^6$ .......................................................... F25J 1/00
[52] U.S. Cl. .............................................................. 62/631
[58] Field of Search ............................... 62/630, 631, 620

[56] References Cited

U.S. PATENT DOCUMENTS

| | | | |
|---|---|---|---|
| 4,411,676 | 10/1983 | Tedder | 62/631 |
| 4,759,786 | 7/1988 | Atkinson et al. | 62/631 |
| 4,897,098 | 1/1990 | Pate et al. | 62/630 |
| 5,346,595 | 9/1994 | Clemmer . | |
| 5,396,000 | 3/1995 | Nappa . | |
| 5,574,192 | 11/1996 | VanDerPuy . | |
| 5,616,819 | 4/1997 | Boyce . | |

FOREIGN PATENT DOCUMENTS

| | | |
|---|---|---|
| 0 467 531 A1 | 6/1991 | European Pat. Off. . |
| 92/20640 | 11/1992 | WIPO . |
| 93/23355 | 11/1993 | WIPO . |
| 97/27163 | 7/1997 | WIPO . |

Primary Examiner—Ronald Capossela
Attorney, Agent, or Firm—Jay P. Friedenson; Marie Collazo

[57] ABSTRACT

The invention provides a method for separating fluorocarbons from mixtures of fluorocarbon and hydrogen fluoride. In particular, the invention provides a method for separating fluorocarbons, such as pentafluoropropane, from azeotropic mixtures of the fluorocarbon and hydrogen fluoride using compositional variations with pressure.

22 Claims, 1 Drawing Sheet

PROCESS FOR SEPARATING HYDROGEN FLUORIDE FROM FLUOROCARBONS

FIELD OF THE INVENTION

The invention relates to methods for separating fluorocarbons from mixtures of fluorocarbon and hydrogen fluoride. In particular, the invention provides a method for separating fluorocarbons, such as pentafluoropropane, from azeotropic mixtures of the fluorocarbon and hydrogen fluoride.

BACKGROUND OF THE INVENTION

Certain processes for manufacturing fluorocarbons result in the production of azeotropic mixtures of the desired fluorocarbon and hydrogen fluoride. Such azeotropic mixtures may be homogeneous or heterogeneous. Although it is difficult to separate the components of any azeotropic mixture, the separation of the components of a homogeneous azeotropic mixture is particularly difficult.

Various methods for separating the fluorocarbon from azeotropic mixtures are known. As one example, extractive distillation using a component dissolvable in the hydrogen fluoride and producing an insoluble liquid phase enriched in the fluorocarbon has been disclosed. However, extractive distillation both adds cost and time and requires a step in which the extracting agent is recovered.

Therefore, a need exists for a method for efficiently separating fluorocarbons from fluorocarbon/hydrogen fluoride azeotropic mixtures. The present invention provides such a method.

DESCRIPTION OF THE INVENTION AND PREFERRED EMBODIMENTS

The present invention provides a convenient and efficient process for separating a fluorocarbon from a fluorocarbon/hydrogen fluoride azeotropic mixture. The process according to the invention provides a process comprising, consisting essentially of, and consisting of the steps of:

(A) distilling a mixture comprising, consisting essentially of, and consisting of at least an azeotropic mixture of a fluorocarbon and hydrogen fluoride at a first pressure to produce a first overhead stream enriched in either the fluorocarbon or the hydrogen fluoride and a first bottoms stream enriched in the other component; and (B) redistilling the first overhead stream at a second pressure to produce a second overhead stream enriched in the component enriched in the first bottoms stream and a second bottoms stream enriched in the component enriched in the first overhead stream.

By "enriched" is meant that there is more of one component of the mixture present relative to the other component when the mixture is compared to the mixture being distilled. By "fluorocarbon" is meant any fluorinated hydrocarbon, including without limitation, hydrochlorofluorocarbons, hydrofluorocarbons, and perfluorocarbons.

Preferred fluorocarbons in the azeotropic mixtures useful in the invention are $C_3$ to $C_5$ alkanes and alkenes containing at least one fluorine atom. Particularly preferred fluorocarbons are the isomers of pentafluoropropane, hexafluoropropane, heptafluoropropane, hexafluorobutane, octafluorobutane, and pentafluorobutene. Most preferred fluorocarbons are 1,1,1,3,3-pentafluoropropane ("HFC-245fa"), 1,1,1,2,2,4-hexafluorobutane ("HFC-356mcfq"), 1,1,1,3,3,4,4,4-octafluorobutane ("HFC-458mfcf"), and 1,1,1,2,2-pentafluorobutene ("HFC-1345").

It is known that the composition of an azeotropic mixture varies with pressure variations in that the weight percentages of the components of the azeotropic mixture will increase or decrease with pressure depending on the nature of the azeotropic mixture. However, it is unpredictable how much the composition of a particular azeotropic mixture will vary and whether two compounds with close boiling points in azeotropic admixture can be separated by distillation taking advantage of the pressure variation effect.

For some fluorocarbon/hydrogen fluoride azeotropic mixtures, the mixture becomes enriched in the fluorocarbon component as pressure increases, as for example the HFC-245fa/hydrogen fluoride azeotropic mixtures. In one embodiment of the invention, directed to such azeotropic mixtures, the first distillation pressure is higher than the second distillation pressure used. One ordinarily skilled in the art will recognize that any convenient lower pressure may be chosen. However, the choice of the higher pressure used will be limited by efficiency in that increasing pressure beyond a certain point may not result in any greater compositional gradients between the lower and higher pressure distillation columns.

Other fluorocarbon/hydrogen fluoride azeotropic mixtures become richer in the fluorocarbon component at the lower pressure. Thus, in another embodiment of the invention, such mixtures are first distilled at the lower pressure and the second distillation is performed at the higher pressure.

The higher distillation pressure generally may range from about 50 to about 400 psia, preferably about 100 to about 250, more preferably about 150 to about 220, psia. The lower distillation pressure generally may range from about 5 psia to about 50 psia, preferably less than about 35, more preferably less than about 25, most preferably less than about 20, psia. Suitable reflux temperatures for the distillations will be readily determinable by one ordinarily skilled in the art considering the specific fluorocarbon/hydrogen fluoride mixture being distilled and the pressure selected.

The azeotropic mixture of fluorocarbon and hydrogen fluoride may be a part of any stream containing the azeotropic mixture, as for example a fluorocarbon manufacturing process stream. Thus, a mixture of reactants, byproducts and reaction intermediates of the process may be present along with the fluorocarbon/hydrogen fluoride mixture. The purification technique of the invention may be accomplished by using a single distillation column operating at a first pressure and then, subsequently at a second pressure with different batches. Preferably, the process is practiced with a series of distillation columns, meaning at least two columns, operating at several different pressures. When a series of columns is used, the process may be carried out either in continuous or batch mode.

FIG. 1 is a schematic view of the novel distillation technique of the invention in which two distillation columns are used in a continuous distillation. In this FIGURE, the distillate or overhead 4 from the low pressure column C2 is recycled back to the high pressure column C1. Alternately, the first distillation column may be operated at low pressure and the second column at high pressure. In this case, the distillate from the high pressure column is recycled to the low pressure column. When the novel distillation technique of the invention is used commercially, it is best to use it in continuous operating mode in order to maximize the yield.

The invention will be clarified further by a consideration of the following, non-limiting examples.

EXAMPLES

Example 1

To a distillation column with thirty stages, column 1, was fed a mixture containing 25 weight percent hydrogen fluoride and 75 weight percent HFC-245fa, simulating the azeotropic mixture that would be encountered in a typical process for preparing HFC-245fa. Column 1 was brought to reflux at a reflux rate of 1000 lbs/hr, a pressure of 141 psia, and reflux temperature of 167° F. The bottoms stream from the column was essentially all hydrogen fluoride.

The column overhead, or distillate, was enriched in HFC-245fa, having a mass fraction ratio of 82:18 of HFC-245fa:hydrogen fluoride. The overhead was transferred to a second column, column 2, with 20 stages and running at 26 psia and 68° F. The overhead from column 2 had a mass flow ratio of 142.5:47.5 of HFC-245fa: hydrogen fluoride. This overhead was recycled to column 1. The bottoms of column 2 was HFC-245fa with only a trace of hydrogen fluoride.

Example 2

A set of experiments was run in a distillation column having 30 plates to determine the actual HFC-245fa/hydrogen fluoride azeotrope composition, a homogeneous composition, at varying pressures. The distillation column was evacuated and charged with 46.9 lb of high purity (>99.9%) HFC-245fa and 15.8 lbs anhydrous hydrogen fluoride to make up a 25.2 weight percent mixture of hydrogen fluoride and HFC-245fa. The column was then brought to total reflux at several pressures and, at each pressure, the column was held at total reflux for between 7–8 hours to ensure that the column reached equilibrium before the overhead was sampled.

Each sample was analyzed to determine hydrogen fluoride content by the following procedure. A vapor sample of the distillation column was condensed into a 150 cc sample cylinder and weighed to two decimal points. 100 mL deionized water was charged to another empty evacuated cylinder and weighed. The contents of the sample cylinder were then transferred to the cylinder containing the deionized water by pressure difference. The deionized water effectively absorbed the hydrogen fluoride to form an aqueous solution. The cylinder containing the deionized water was weighed to determine the amount of sample transferred. The cylinder was then chilled for approximately ½ hr. The contents of the cylinder were then drained by gravity into a plastic bottle forming an aqueous and organic layer. The plastic bottle was then placed in a freezer for at least 2 h and the layers were subsequently phase separated and the weight of each layer was recorded. The aqueous layer was then titrated using 1.0N sodium hydroxide and the weight percentage of hydrogen fluoride calculated. The results, shown on Table 1 below show a decreasing hydrogen fluoride content with increasing pressure.

TABLE 1

| Pressure (psig) | 25 | 100 | 125 | 150 | 175 | 200 | 225 |
|---|---|---|---|---|---|---|---|
| Reflux Temp (°C.) | 33 | 67 | 74 | 80 | 86 | 91 | 95 |
| Cyl. + $H_2O$ + Sample Wt (g) | 1145.16 | 1180.86 | 1185.7 | 1137.09 | 1156.62 | 1147.23 | 1143.25 |
| Cyl. + $H_2O$ Wt. (g) | 1088.75 | 1090.68 | 1090.53 | 1090.7 | 1076.58 | 1092.44 | 1096.93 |
| Wt. Column Sample | 56.41 | 90.18 | 95.17 | 46.39 | 80.04 | 54.79 | 46.32 |
| Cyl. Wt. (g) | 995.59 | 996.16 | 994.9 | 995.88 | 994.76 | 994.92 | 996.22 |
| Water Wt. (g) | 93.16 | 94.52 | 95.63 | 94.82 | 81.82 | 97.52 | 100.71 |
| HF Wt % Aq. Phase | 10.4 | 12.6 | 12.7 | 6.5 | 11.9 | 7.1 | 5.9 |
| Aq. Phase Wt (g) | 104.0 | 108.1 | 109.5 | 101.4 | 92.9 | 105.0 | 107.0 |
| Wt. % HF in Column. Sample | 19.17 | 15.11 | 14.62 | 14.21 | 13.81 | 13.60 | 13.63 |

Example 3

The vapor equilibrium measurement of HFC-356mcfq and hydrogen fluoride is shown in Table 2 below at 0 and 20° C. The shift in the homogeneous azeotropic composition, from 41.3 to 33 weight percent, with temperature or pressure indicates that HFC-356mcfq can be separated from hydrogen fluoride with the process of the invention as in Example 1.

TABLE 2

| Temp. (°C.) | Press. (psia) | Wt. % HFC-356 mcfq (liquid) | Wt. % HFC-356 mcfq (vapor) |
|---|---|---|---|
| −0.4 | 7.0 | 41.0 | 41.3 |
| 19.8 | 15.5 | 33.3 | 33.5 |

Example 4

The data in Table 3 below show the vapor-liquid-liquid compositions at two temperatures and pressures of HFC-458mfcf/hydrogen fluoride. The shift in composition with temperature or pressure shows that HFC-458mfcf can be separated from hydrogen fluoride in this heterogeneous azeotrope using the process of Example 1. In such compositions, the liquid phase is composed of two layers with different compositions.

TABLE 3

| Temp. (°C.) | Press. (psia) | Wt. % HF Bottom Layer | Wt. % HF Upper Layer | Wt. % HF Vapor Layer |
|---|---|---|---|---|
| −10.7 | 4.3 | 3.0 | 64.9 | 76.9 |
| 60.0 | 55.5 | 25.5 | 27.7 | 51.8 |

Example 5

The data of Table 4 below shows the vapor-liquid-liquid compositions of HFC-1345/hydrogen fluoride at two temperatures and pressures. The shift in composition with temperature or pressure shows that HFC-1345 can be separated from hydrogen fluoride in this heterogeneous azeotrope using the process of Example 1.

TABLE 4

| Temp. (°C.) | Press. (psia) | Wt. % HF Bottom Layer | Wt. % HF Upper Layer | Wt. % HF Vapor Layer |
|---|---|---|---|---|
| −0.4 | 18.8 | 1.5 | 53.3 | 14.4 |
| 60.1 | 131.7 | 28.4 | 28.5 | 7.2 |

What is claimed is:

1. A process comprising the steps of:
   (A) distilling a mixture comprising at least an azeotropic mixture of a fluorocarbon and hydrogen fluoride at a first pressure to produce a first overhead stream enriched in either the fluorocarbon or the hydrogen fluoride and a first bottoms stream enriched in the other component; and
   (B) redistilling the first overhead stream at a second pressure to produce a second overhead stream enriched in the component enriched in the first bottoms stream and a second bottoms stream enriched in the component enriched in the first overhead stream.

2. The process of claim 1 wherein the fluorocarbon is a $C_3$ to $C_5$ alkane or alkene containing at least one fluorine atom.

3. The process of claim 1 wherein the fluorocarbon is selected from the group consisting of isomers of pentafluoropropane, hexafluoropropane, heptafluoropropane, hexafluorobutane, octafluorobutane, and pentafluorobutene.

4. The process of claim 3 wherein the fluorocarbon is selected from the group consisting of 1,1,1,3,3-pentafluoropropane, 1,1,1,2,2,4-hexafluorobutane, 1,1,1,3,3,4,4,4-octafluorobutane, and 1,1,1,2,2-pentafluorobutene.

5. The process of claim 4 wherein the fluorocarbon is 1,1,1,3,3-pentafluoropropane.

6. The process of claim 4 wherein the fluorocarbon is 1,1,1,2,2,4-hexafluorobutane.

7. The process of claim 4 wherein the fluorocarbon is 1,1,1,3,3,4,4,4-octafluorobutane.

8. The process of claim 4 wherein the fluorocarbon is 1,1,1,2,2-pentafluorobutene.

9. The process of claim 1 wherein the first distillation pressure is from about 50 to about 400 psia and the second distillation pressure is from about 5 psia to about 50 psia.

10. The process of claim 1 wherein the first distillation pressure is from about 5 psia to about 50 psia and the second distillation pressure is from about 50 to about 400 psia.

11. A process comprising the steps of:
    (A) distilling a mixture comprising at least an azeotropic mixture of a $C_3$ to $C_5$ alkane or alkene containing at least one fluorine atom and hydrogen fluoride at a first pressure to produce a first overhead stream enriched in either the fluorocarbon or the hydrogen fluoride and a first bottoms stream enriched in the other component; and
    (B) redistilling the first overhead stream at a second pressure to produce a second overhead stream enriched in the component enriched in the first bottoms stream and a second bottoms stream enriched in the component enriched in the first overhead stream
    wherein the first distillation pressure is from about 50 to about 400 psia and the second distillation pressure is from about 5 psia to about 50 psia.

12. The process of claim 11 wherein the $C_3$ to $C_5$ alkane or alkene is selected from the group consisting of 1,1,1,3,3-pentafluoropropane, 1,1,1,2,2,4-hexafluorobutane, 1,1,1,3,3,4,4,4-octafluorobutane, and 1,1,1,2,2-pentafluorobutene.

13. The process of claim 12 wherein the fluorocarbon is 1,1,1,3,3-pentafluoropropane.

14. The process of claim 12 wherein the fluorocarbon is 1,1,1,2,2,4-hexafluorobutane.

15. The process of claim 12 wherein the fluorocarbon is 1,1,1,3,3,4,4,4-octafluorobutane.

16. The process of claim 12 wherein the fluorocarbon is 1,1,1,2,2-pentafluorobutene.

17. A process comprising the steps of:
    (A) distilling a mixture comprising at least an azeotropic mixture of a $C_3$ to $C_5$ alkane or alkene containing at least one fluorine atom and hydrogen fluoride at a first pressure to produce a first overhead stream enriched in either the fluorocarbon or the hydrogen fluoride and a first bottoms stream enriched in the other component; and
    (B) redistilling the first overhead stream at a second pressure to produce a second overhead stream enriched in the component enriched in the first bottoms stream and a second bottoms stream enriched in the component enriched in the first overhead stream
    wherein the first distillation pressure is from about 5 psia to about 50 psia and the second distillation pressure is from about 50 to about 400.

18. The process of claim 17 wherein the $C_3$ to $C_5$ alkane or alkene is selected from the group consisting of 1,1,1,3,3-pentafluoropropane, 1,1,1,2,2,4-hexafluorobutane, 1,1,1,3,3,4,4,4-octafluorobutane, and 1,1,1,2,2-pentafluorobutene.

19. The process of claim 18 wherein the fluorocarbon is 1,1,1,3,3-pentafluoropropane.

20. The process of claim 18 wherein the fluorocarbon is 1,1,1,2,2,4-hexafluorobutane.

21. The process of claim 18 wherein the fluorocarbon is 1,1,1,3,3,4,4,4-octafluorobutane.

22. The process of claim 18 wherein the fluorocarbon is 1,1,1,2,2-pentafluorobutene.

* * * * *